(12) United States Patent
Klingenbeck-Regn

(10) Patent No.: US 6,512,808 B2
(45) Date of Patent: Jan. 28, 2003

(54) METHOD FOR OPERATING A COMPUTED TOMOGRAPHY APPARATUS

(75) Inventor: Klaus Klingenbeck-Regn, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 4 days.

(21) Appl. No.: 09/742,152

(22) Filed: Dec. 20, 2000

(65) Prior Publication Data

US 2001/0004393 A1 Jun. 21, 2001

(30) Foreign Application Priority Data

Dec. 20, 1999 (DE) .......................................... 199 61 524

(51) Int. Cl.⁷ ................................................ A61B 6/03
(52) U.S. Cl. ........................................ 378/18; 378/162
(58) Field of Search .......................... 378/4, 8, 15, 16, 378/18, 20, 95, 162, 207, 99

(56) References Cited

U.S. PATENT DOCUMENTS

| 4,624,007 A | * | 11/1986 | Muranushi | ...................... 378/4 |
| 5,212,717 A | * | 5/1993 | Hada | .............................. 378/4 |
| 6,151,378 A | * | 11/2000 | Rasche et al. | ................. 378/4 |
| 6,243,436 B1 | * | 6/2001 | Hahn et al. | ..................... 378/4 |

* cited by examiner

Primary Examiner—Drew A. Dunn
Assistant Examiner—Therese Barber
(74) Attorney, Agent, or Firm—Schiff Hardin & Waite

(57) ABSTRACT

In a method for the operation of a CT apparatus with which volume data for a volume region of an examination subject are registered, markings for identifying reconstruction regions are mixed into an x-ray shadowgram containing the volume region. The reconstruction of image data with respect to each reconstruction region ensues taking reconstruction parameters allocated to the respective reconstruction region into consideration.

11 Claims, 3 Drawing Sheets

METHOD FOR OPERATING A COMPUTED TOMOGRAPHY APPARATUS

BACKGROUND OF THE INVENTION

1. Field of the Invention

The present invention is directed to a method for the operation of a computed tomography (CT) apparatus with which volume data for a volume region of an examination subject can be registered.

2. Description of the Prior Art

Before the definition of a region for which volume data are to be registered, for example with a spiral scan, an x-ray shadowgram (topogram) is usually registered, with reference to which the scan region of the following spiral scan is graphically defined. The definition of a scan region ensues by graphic marking of a generally rectangular region in the x-ray shadowgram that encompasses the region of interest of the examination subject. The length of the rectangle defines the length of the spiral scan; the width of the rectangle defines the width of the field of view shown in the CT image.

In the case of multiple spiral scans, the above procedure is repeatedly applied for defining each spiral scan.

SUMMARY OF THE INVENTION

An object of the present invention is to provide a method of the type described above that makes it easy for an operator to acquire the respectively desired, diagnostic information.

The above object is achieved in a method for operating a computed tomography apparatus in accordance with the principles of the present invention, wherein volume data for a volume region of an examination subject are registered, wherein an x-ray shadowgram of a region of an examination subject containing the volume region is produced, and a plurality of markings are mixed into the x-ray shadowgram for identifying reconstruction regions in the volume region for which image data are to be reconstructed from the volume data, and wherein at least one reconstruction parameter is allocated to each of the reconstruction regions, and wherein image data are reconstructed for each of the reconstruction regions employing the (at least one) reconstruction parameter allocated to the respective reconstruction region.

It is thus possible to mark a number of regions within, for example, the volume data registered in a spiral scan, from which a number of regions a reconstruction of image data then ensues with reconstruction parameters that are appropriate for the respective region of the examination subject, for example the slice thickness underlying the reconstruction, referred to as the thick reconstructed slice, the convolution kernel to be applied in the reconstruction, etc.

The invention thus facilitates the clinical use of CT apparatuses, particularly in applications, on the basis of a facilitated operation and optimized executive sequence, for which it is necessary to reconstruct sub-sections of an organ, particularly for the diagnosis of, for example, an organ with a different slice thickness than other subsections of the same organ. This is because, in accordance with the invention, the reconstruction ensues on the basis of volume data acquired during a single spiral scan, with marking of the reconstruction regions simultaneously ensuing in a single work step and in a single x-ray shadowgram.

In a version of the invention, the data required for the production of the x-ray shadowgram are registered before the registration of the volume data, and the registration of the volume data ensues after the identification of the reconstruction regions, so that volume data with respect to each reconstruction region are available. The marking of the reconstruction regions thus ensues prospectively before the registration of the volume data.

Alternatively, in another version of the invention the marking of reconstruction regions ensues for volume data already registered, on the basis of an x-ray shadowgram belonging to the volume data already registered; and the reconstruction of image data corresponding to the reconstruction regions ensues based on the volume data already registered. This means that a retrospective definition of reconstruction regions is also possible insofar as volume data are present. If a shadowgram belonging to the volume data is not already present, this can be produced by acquiring the data required for the production of the x-ray shadowgram from the volume data that have already been registered.

In a preferred embodiment of the invention, the volume data are registered in the form of a spiral scan.

In a further embodiment of the invention, when a number of reconstruction regions are marked, these can at least partially overlap one another. This offers the advantage that regions of the examination subject contained in a number of reconstruction regions are not multiply scanned and thereby need not be charged with x-radiation.

In another embodiment of the invention, at least the slice thickness and/or convolution kernel can be prescribed as reconstruction parameters.

A modern multi-slice CT apparatus, i.e. a CT apparatus with a detector system formed by a number of lines of detector elements, is able to scan volumes with high axial resolution, i.e. narrow collimation (small slice thickness of the slices of the examination subject scanned with the individual lines of the detector system) in a single spiral scan. Volume data result from this scan from which, for example, images of thin or thick slices can be subsequently reconstructed. Thus, it is possible for the user to acquire different diagnostic information from volume data registered in a single spiral scan with tight collimation: thinner slices in order to acquire information about highcontrast structures, for example bones, vessels filled with contrast agent, air-containing bronchia or prepared intestinal material, and thicker slices in order to be able to acquire information about low-contrast structures, for example soft tissue parts.

A typical example of a spiral scan is a scan of the skull with a collimation of 4*1 mm. The radiologist needs slice thicknesses of 3 mm or 4 mm for the base of the skull; slice thicknesses of 5 mm through 8 mm are standard for the cerebellum. Given simultaneous CTA (CT angiography), the thinnest slices of 1 mm are required, for example for the presentation of the circulus Willisis (Circle of Willis).

Similar demands arise in the examination of other organs such as the lung, with high-resolution images having a 1 mm slice thickness, and standard images having a 5 mm slice thickness or CTA of the abdomen or examination of the entire aorta with the various arterial branchings.

Depending on the clinical demands, the reconstruction ranges can overlap to form a spiral range or can be nested inside one another.

When, as in a multi-phase liver examination, a number of spiral scans are implemented, method can be employed in the aforementioned way with respect to each and every individual spiral scan.

DESCRIPTION OF THE PREFERRED EMBODIMENTS

Figure 1:
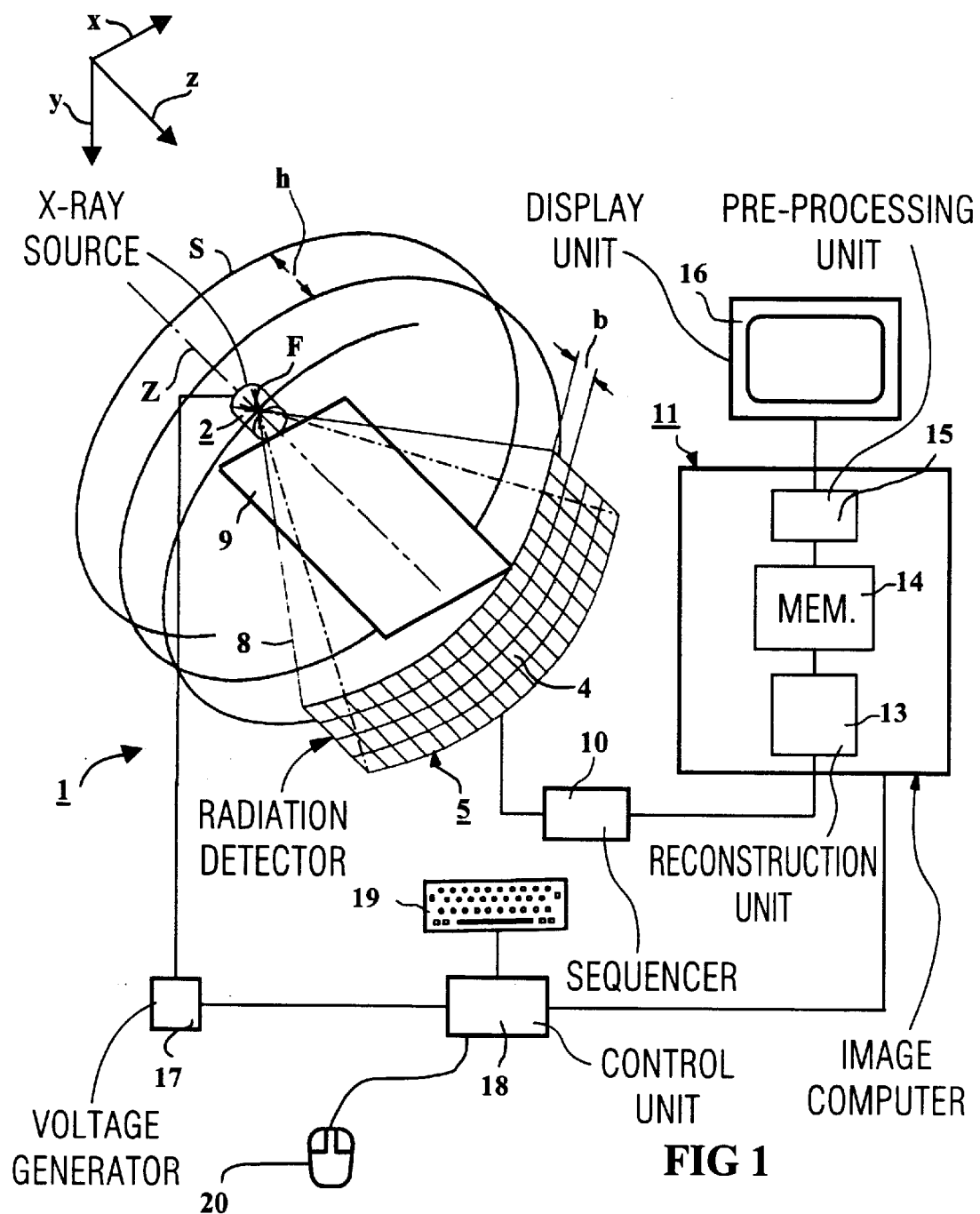
FIG. 1 is a partially perspective, partially block circuit diagram presentation of a CT apparatus suitable for the implementation of the inventive method.
Figure 2:
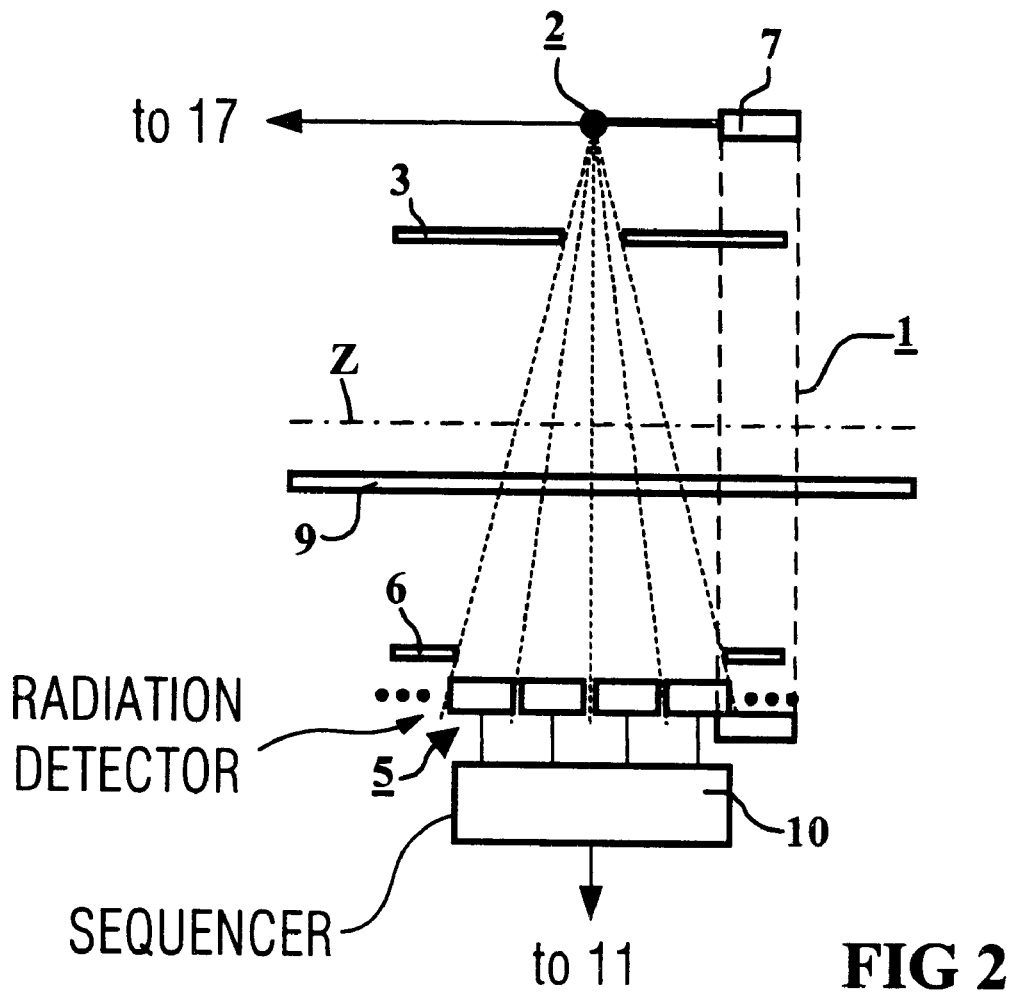
FIG. 2 is a longitudinal section through the apparatus according to FIG. 1.

FIGS. 1 and 2 show a multi-slice CT apparatus of the third generation suitable for the implementation of the inventive method. The measuring arrangement thereof—generally referenced 1—includes an x-ray source 2 overall having a source-proximate radiation diaphragm 3 (FIG. 2) preceding it. The measuring arrangement 2 also includes a detector system 5 fashioned as a planar array of a number of rows and columns of detector elements—one of these is referenced 4 in FIG. 1—having a detector-proximate radiation diaphragm 6 (FIG. 2) preceding it. The x-ray source 2 together with the radiation diaphragm 3, and the detector system 5 together with the radiation diaphragm 6, are mounted opposite one another on a rotating frame 7 in the way shown in FIG. 2 such that a pyramidal x-ray beam emanating from the x-ray source 2 during operation of the CT apparatus and gated by the variable radiation diaphragm 3 strikes the detector system 5, the edge rays of this x-ray beam being referenced 8. The radiation diaphragm 6 is set, corresponding to the cross-section of the x-ray beam set with the radiation diaphragm 3, so that only that region of the detector system 5 is activated that can be directly struck by the x-ray beam. In the operating condition shown in FIGS. 1 and 2, there are four rows of detector elements. The fact that further rows of detector elements covered by the radiation diaphragm 6 are present is indicated by dotted in FIG. 2.

The rotating frame 7 can be placed into rotation around a system axis Z, with a drive means (not shown). The system axis Z proceeds parallel to the z-axis of a spatial rectangular coordinate system shown in FIG. 1.

The columns of the detector system 5 likewise proceed in the direction of the zaxis, whereas the rows, whose width b extends in the direction of the z-axis and amounts, for example, to 1 mm, proceed transversely relative to the system axis Z ,or to the z-axis.

In order to be able to introduce an examination subject, for example a patient, into the beam path of the x-ray beam, a positioning arrangement 9 is provided that is displaceable parallel to the system axis Z, i.e. in the direction of the z-axis.

For registering volume data of an examination subject situated on the positioning arrangement 9, for example a patient, scanning of the examination subject ensues by registering a number of projections from various projection directions given motion of the measurement unit 1 around the system axis Z. The data supplied by the detector system 5 thus represent a number of projections.

During the continuous rotation of the measurement unit 1 around the system axis Z, the positioning arrangement 9 is simultaneously continuously displaced in the direction of the system axis Z relative to the measuring unit 1, with a synchronization between the rotational movement of the rotating frame 7 and of the translational movement of the positioning means 9 so that the ratio of translational to rotational speed is constant. This constant ratio can be set by selecting a value for the translation h of the positioning arrangement 9 per revolution of the rotating frame 7 that guarantees a complete scan of the volume of interest of the examination subject. The focus F of the x-ray source 2 thus moves—as seen proceeding from the examination subject— on a spiral path (referenced S in FIG. 1) around the system axis Z, for which reason the described type of registration of volume data is referred to as spiral scan. The volume data thereby supplied by the detector elements of each row of the detector system 5, represent projections respectively allocated to that row of the detector system 5 and to a specific position relative to the system axis Z. The data are read out in parallel from the respective rows, and are serialized in a sequencer 10 and are transmitted to an image computer 11.

After a pre-processing of the volume data in a pre-processing unit 15 of the image computer 11, the resultant data stream proceeds to a memory 14 wherein the volume data corresponding to the data stream are stored.

The image computer 11 contains a reconstruction unit 13 that reconstructs image data, for example in the form of tomograms of desired slices of the examination subject, from the volume data in conformity with methods well-known to those skilled in the art. The image data reconstructed by the reconstruction unit 13 are stored in the memory 14 and can be displayed at the display unit 16, for example a video monitor, connected to the image computer 11.

The x-ray source 2, for example an x-ray tube, is supplied with the necessary voltages and currents by a voltage generator unit 17. In order to be able to set these parameters to the respectively needed values, the voltage generator unit 17 has a control unit 18 with keyboard 19 and mouse 20 allocated thereto that allows the necessary settings to be undertaken.

The rest of the operation and control of the CT apparatus also ensues with the control unit 18 and the keyboard 19 as well as the mouse 20, this being illustrated by the control unit 18 being connected to the image computer 11.

In order to limit the registration of volume data to the diagnostically necessary region, and thus to save the examination subject from unnecessary x-radiation, an x-ray shadowgram of the diagnostically relevant region of the examination subject is prepared before the registration of the volume data. With an activated x-ray source but without rotation of the measuring unit 1 around the system axis Z, displacement of the positioning arrangement 6 in the direction of the system axis 7 relative to the measuring unit 1 is implemented to an extent for this purpose that is required for the acquisition of the diagnostically relevant region of the examination subject. The output data of the detector system 5 thereby obtained are transmitted in serial form to the image computer 11 which calculates an x-ray shadowgram (topogram) from these data according to known algorithms, displays this on the display unit 16 and, if requested, stores it in the memory 14. The display of an x-ray shadowgram is illustrated in FIG. 3, which shows the picture screen of the display unit 16.

Figure 3:
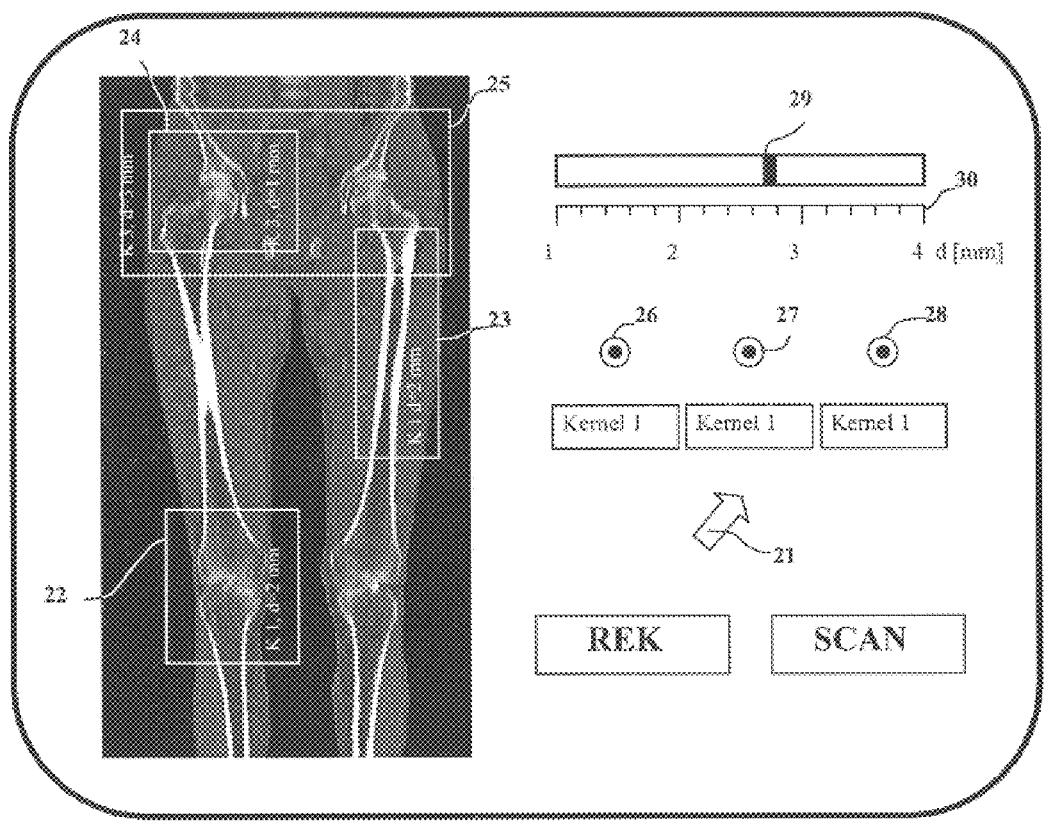
FIG. 3 shows the user interface of the CT apparatus according to FIGS. 1 and 2 with displays for the implementation of the inventive method.

As can also be seen from FIG. 3, it is possible using the mouse 20—the appertaining curser is referenced 21—to mark rectangular reconstruction regions, for example 22, 23, 24 and 25, in the x-ray shadowgram with respect to which volume data allowing the reconstruction of image data are to be registered.

As soon as an operator, using the cursor 21 upon actuation of the left button of the mouse 20, activates a corresponding operating element surface (icon) referenced SCAN and shown on the picture screen, the control unit 18 uses the position and size of the marked reconstruction regions 22 through 25 to calculate the start and end points for the displacement of the positioning arrangement 9 in the direction of the system axis Z. This is required in order to be able to register—during the course of one spiral scan—the volume data that allow the reconstruction of image data for the marked reconstruction regions 22 through 25. The control unit 18 initiates the implementation of the corresponding spiral scan.

Before or after the implementation of the spiral scan, an operator can allocate individual reconstruction parameters to the individual reconstruction regions 22 through 25 by actuating corresponding operating elements displayed on the picture screen.

As reconstruction parameters, FIG. 3—as an example—shows the convolution kernel (kernel 1, kernel 2, kernel 3) to be employed in the reconstruction of the respective reconstruction region and the reconstructive slice thickness d to form the basis for the reconstruction of the respective region. The reconstructed slice thickness d is the half-width value of the slice sensitivity profile, and thus that slice thickness from which the data contained in a reconstructed tomogram were obtained.

When a corresponding operating element surface referenced REK and shown on the picture screen is now activated with the cursor 21, the image computer 11 reconstructs image data with respect to the reconstruction regions 22 through 25 from the volume data previously registered during the course of the spiral scan according to algorithms with which those skilled in the art are familiar. This is based upon the reconstruction parameter allocated to the respective reconstruction region.

The allocation of reconstruction parameters to a reconstruction region 22 through 25 occurs such that the cursor 21 is moved to the respective reconstruction region, for example, the reconstruction region 23, and this reconstruction region is placed into an activated condition by actuation of the right-hand button of the mouse 20. Then, after selection of a convolution kernel and a reconstructed slice thickness d, these reconstruction parameters are allocated to the respective reconstruction region.

The allocation of the reconstruction parameters to the respectively activated reconstruction region occurs—as regards the convolution kernel—by moving the cursor 21 to the button 26 through 28 allocated to the desired convolution kernel (kernel 1 through kernel 3) and this is activated by clicking the left key of the mouse 20.

As regards the reconstructed slice thickness, this is set to the desired value by displacing a slide 29 on a scale 30. The slide 29 can be set by moving the cursor 21 onto the slide 29, which is shifted upon actuation of the left key of the mouse 20.

As can be seen from FIG. 3, the reconstruction parameters allocated to the reconstruction regions 22 through 25 are displayed in the x-ray shadowgram within the reconstruction regions 22 through 25.

As can also be seen from FIG. 3, reconstruction regions can be defined that, for example like the reconstruction regions 22 and 24, are completely separated from one another. Reconstruction regions also can partially overlap, as is the case given the reconstruction regions 23 and 25. Moreover, reconstruction regions can be defined that completely overlap, i.e. are nested inside one another, as is the case given the reconstruction regions 24 and 25.

In the case of the above-described operating mode of the apparatus, the marking of the reconstruction regions ensues, so to speak, prospectively on the basis of the xray shadowgram before the registration of the volume data.

When volume data are already present with respect to a diagnostically relevant region, for example stored in the memory 14, a retrospective procedure is also possible in a second operating mode, insofar as an x-ray shadowgram belonging to the volume data is likewise available or can be derived from the volume data according to a well-known method. In the case of such a retrospective procedure, the x-ray shadowgram belonging to the volume data or the x-ray shadowgram determined from the volume data is displayed in order to mark the desired reconstruction regions therein and to allocate reconstruction parameters to the marked reconstruction regions, whereupon the corresponding image data are reconstructed on the basis of the volume data that already exist. The described, retrospective procedure makes it possible—during the course of a diagnosis—to reconstruct image data on the basis of an existing volume dataset with respect to different reconstruction regions with appertaining reconstruction parameters, or to reconstruct image data with modified reconstruction parameters on the basis of reconstruction regions that were already previously reconstructed, without a renewed registration of volume data be required together with the radiation stress on the examination subject connected therewith.

The inventive method thus allows different reconstruction regions having the respectively suitable reconstruction parameters to be defined in volume data in a graphic way in a simple, flexible and clear fashion, these volume data, for example, being or having been registered with a spiral scan.

In the exemplary embodiment, the structure of the image computer 11 is described with the pre-processing unit 12 and the reconstruction unit 13 as hardware components. This can in fact be the case. As a rule, however, these components are realized by software modules that run on a universal computer provided with the required interfaces and that, in a departure from FIG. 1, can also assume the function of the control unit 18, which is then superfluous.

The CT apparatus in the described exemplary embodiment has a detector system with five rows whose widths measured in the z-direction are of the same size and, for example, amounts to 1 mm. In a departure therefrom, a detector system can be provided within the scope of the invention with rows having different widths. Thus, for example, two inner rows can be provided each having a width of 1 mm and a respective row having a width of 2 mm can be provided at each side thereof.

In the described exemplary embodiment, the relative motion between the measuring unit 1 and the positioning arrangement 9 is produced by displacing the positioning arrangement 9. There is also the possibility within the scope of the invention to leave the positioning arrangement 9 stationary and to instead displace the measuring unit 1. Moreover, there is also the possibility within the scope of the invention to produce the relative motion by displacing both the measuring unit 1 as well as the positioning arrangement 9.

A CT apparatus of the third generation is described in conjunction with the exemplary embodiments, i.e. the x-ray source and the detector system are displaced in common around the system axis during the image generation. The invention, however, also can be employed in conjunction with a CT apparatus of the fourth generation wherein only the x-ray source is displaced around the system axis and interacts with a stationary detector ring, with the detector system being a planar array of detector elements.

The inventive method also can be employed in a CT apparatus of the fifth generation, i.e. a CT apparatus wherein the x-rays emanate not only from one focus but from a number of foci of one or more x-ray sources displaced around the system axis, and the detector system is a planar array of detector elements.

The CT apparatus employed in conjunction with the above-described exemplary embodiments has a detector system with detector elements arranged in the fashion of an orthogonal matrix. The invention, however, also can be employed in conjunction with a CT apparatus having a detector system with detector elements arranged as a planar array in some other fashion.

The above-described exemplary embodiments are directed to the medical application of the inventive method. The invention, however, also can be employed beyond medicine, for example, in baggage inspection or in the inspection of materials.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a computed tomography apparatus wherein volume data for an overall volume region of an examination subject are registered, comprising the steps of:
    (a) producing an x-ray shadowgram of a region of an examination subject containing the overall volume region;
    (b) mixing a plurality of markings for respectively identifying reconstruction sub-regions in said overall volume region for which image data are to be reconstructed from said volume data;
    (c) allocating at least one different reconstruction parameter to each of said reconstruction sub-regions; and
    (d) reconstructing image data for each of said reconstruction sub-regions employing the at least one reconstruction parameter allocated to the respective reconstruction sub-region.

2. A method as claimed in claim 1 wherein step (c) comprises allocating at least one different reconstruction parameter selected from the group consisting of slice thickness and convolution kernel to each of said reconstruction sub-regions.

3. A method as claimed in claim 1 wherein step (b) comprises mixing a plurality of markings respectively identifying reconstruction sub-regions which at least partially overlap.

4. A method for operating a computed tomography apparatus comprising the steps of:
    (a) obtaining shadowgram data from an examination subject containing an overall volume region from which a reconstructed image is to be obtained, and generating and displaying an x-ray shadowgram from said shadowgram data;
    (b) mixing a plurality of markings into the displayed shadowgram for respectively identifying reconstruction sub-regions within said overall volume region for which said reconstructed image is to be produced;
    (c) registering volume data from said volume region dependent on said reconstruction sub-regions identified in said shadowgram;
    (d) allocating at least one different reconstruction parameter to each of said reconstruction sub-regions; and
    (e) reconstructing image data from said volume data for each of said reconstruction sub-regions employing the at least one reconstruction parameter respectively allocated to the reconstruction sub-region.

5. A method as claimed in claim 4 wherein step (c) comprises registering said volume data with a spiral scan.

6. A method as claimed in claim 4 wherein step (b) comprises mixing a plurality of markings respectively identifying reconstruction sub-regions which at least partially overlap.

7. A method as claimed in claim 4 wherein step (d) comprises allocating at least one different reconstruction parameter selected from the group consisting of slice thickness and convolution kernel to each of said reconstruction sub-regions.

8. A method for operating a computed tomography apparatus comprising the steps of:
    (a) registering volume data for an overall volume region of an examination subject;
    (b) from said volume data, producing and displaying an x-ray shadowgram containing said overall volume region;
    (c) in the displayed shadowgram, mixing in a plurality of markings identifying reconstruction sub-regions in said overall volume region for which image data are to be reconstructed;
    (d) allocating at least one different reconstruction parameter to each of said reconstruction sub-regions; and
    (e) reconstructing image data from said volume data for each of said reconstruction sub-regions employing the at least one reconstruction parameter respectively allocated to the reconstruction sub-region.

9. A method as claimed in claim 8 wherein step (a) comprises registering said volume data with a spiral scan.

10. A method as claimed in claim 8 wherein step (c) comprises mixing a plurality of markings respectively identifying reconstruction sub-regions which at least partially overlap.

11. A method as claimed in claim 8 wherein step (d) comprises allocating at least one different reconstruction parameter selected from the group consisting of slice thickness and convolution kernel to each of said reconstruction sub-regions.

* * * * *